United States Patent [19]

Hochberg et al.

[11] Patent Number: 4,780,420

[45] Date of Patent: Oct. 25, 1988

[54] PROGESTERONE RECEPTOR LIGANDS

[75] Inventors: Richard Hochberg, Guilford, Conn.; William Rosner, New York; Robert Hoyte, Flushing, both of N.Y.

[73] Assignee: Yale University, New Haven, Conn.

[21] Appl. No.: 782,068

[22] Filed: Sep. 30, 1985

[51] Int. Cl.$^4$ ............... G01N 33/566; G01N 33/567; C07J 1/00; C07J 3/00
[52] U.S. Cl. .................................. 436/503; 436/501; 436/504; 436/815; 436/817; 260/397; 260/397.4; 260/397.5; 514/169; 514/178
[58] Field of Search ............... 436/501, 503, 504, 815, 436/817; 514/169, 178; 260/397, 397.4, 397.5

[56] References Cited

U.S. PATENT DOCUMENTS

| | | | |
|---|---|---|---|
| 3,498,975 | 3/1970 | Oberster et al. | 260/397.4 |
| 4,321,208 | 3/1982 | Sahadevan | 260/397.5 |
| 4,465,676 | 8/1984 | Hochberg | 260/397.5 |
| 4,541,957 | 9/1985 | Nakatsuka et al. | 260/397.5 |

FOREIGN PATENT DOCUMENTS 0137434  4/1985  European Pat. Off. .

OTHER PUBLICATIONS

Pichon, M. F., et al., Cancer Research 37: 464–471, (1977).
Hanson, R. N., et al., Journ. Nucl. Med., 23: 431–436, (1982).
"Receptor-Binding Radiotracers: A Class of Potential Radiopharmaceuticals", by William C. Eckelman et al., J. Nucl. Med. 20, 350–357 (1979).
"Radiochemistry and Radiopharmaceuticals", by Mazaitis, J. K., et al., J. Nucl. Med. 21, 142–146 (1980).
"Iodohexestrols. II. Characterization of the Binding and Estrogenic Activity of Iodinated Hexestrol Derivatives, in Vitro and in Vivo", by Katzenellenbogen, J. A., et al., Biochemistry 14, 1742–1750 (1975).
"Iodoestrogens, Syntheses, and Interaction with Uterine Receptors", by Arunachalam, T., et al., J. Biol. Chem. 254, 5900–5905 (1979).
"Iodine-125-Labeled Estradiol: A Gamma-Emitting Analog of Estradiol That Binds to the Estrogen Receptor", by Hochberg, R. Science 205, 1138–1140 (1979).
"Synthesis of 16α-[$^{125}$I] Iodo-5-Dihydroteststerone . . . ", by Hoyte, R. M., J. Steroid Biochem. 16, 621–628 (1982).
"17β-Carboxamide Steroids are a New Class of Glucocorticoid Antagonists", by Rousseau, G. G., et al., Nature 279, 158–160 (1979).
"Synthesis and Evaluation of Potential Radioligands for the Progesterone Receptor", by Hoyte, R. M. et al., J. Med. Chem. 28, 1695–1699 (1985).

*Primary Examiner*—Robert J. Warden
*Assistant Examiner*—Jack Spiegel
*Attorney, Agent, or Firm*—Ostrolenk, Faber, Gerb & Soffen

[57] ABSTRACT

Radiodinated and non-radiodinated 16α-iodo- and 17α-(2-iodovinyl)-19-nortestosterones are prepared and are used in progesterone receptor assays.

18 Claims, 2 Drawing Sheets

[$^{125}$I]E-IVNT ○ $Ka = 1.25 \times 10^9$ L/M, BINDING CAPACITY 942 pM
[$^3$H]R-5020 ● $Ka = 1.02 \times 10^9$ L/M, BINDING CAPACITY 1100 pM

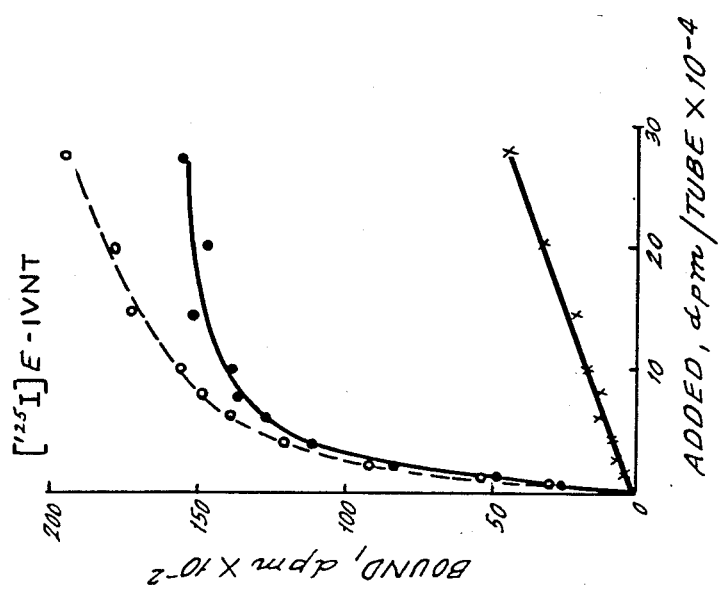
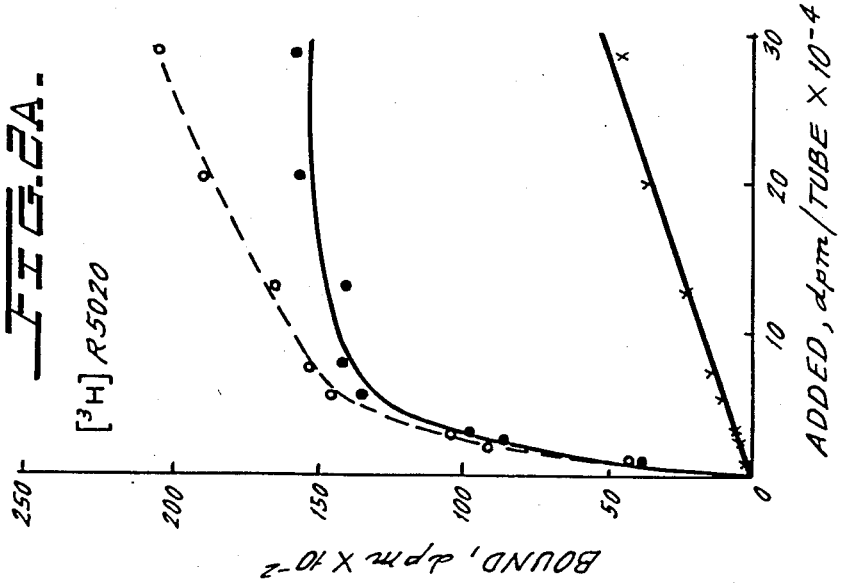

PROGESTERONE RECEPTOR LIGANDS

This invention was made with Government support under grants CA 29591, CA 37799, RR 08180 and AM 28562 from the NIH. The U.S Government has certain rights in this invention.

BACKGROUND OF THE INVENTION

The synthesis of γ-emitting halogenated steroids is not unusually difficult, but the synthesis of such compounds which also have biological activity has, for the most part, resisted intensive efforts. The complex information which is encoded within the steroid hormone molecule is contained within such a small structure that analogs labelled, for example, with the useful isotopes of iodine, are usually biologically inactive. The radiohalogen is so bulky compared to the steroid nucleus that it interferes with the exquisitely sensitive interaction of the hormone with its receptor. These difficulties have limited the development of the useful biological and clinical probes of hormone action and to date, the only radioiodonated, biologically active steroids that have been synthesized are estrogens.

Hochberg in U.S. Pat. No. 4,465,676 describes 16α-radiohalogenated-3,17β-dihydroxysteroidal estrogens, including the 16α-iodo analog of estradiol, and their use in estrogen receptor assays, radioimmunoassays, in vivo imaging of tissue having estrogen receptor activity, and for therapeutic treatment of tumors which have estrogen receptor activity. Additionally, the E-17α-[2-iodovinyl]analogs of estradiol have been prepared which bind to the estrogen receptor and concentrate in estrogen target tissues. See Hansen et al., J Nuclear Med. (1982), 23, 431 and Jogoda et al., J. Nuclear Med. (1984), 25, 472.

The quantification of the estrogen receptor is an important adjunct in determining therapy in patients with carcinoma of the breast and 16α-[$^{125}$I]iodoestradiol is frequently used for the active detection of this trace protin. More recently, it has become clear that the measurement of the progesterone receptor (an estrogen-induced protein) in addition to the estrogen receptor, yields more accurate guidelines for hormonal therapy of breast cancer. Clark et al., Breast Cancer Res. Treat. (1983), 3, 157.

A number of steroids have been prepared as potential ligands for the progesterone receptor and tested for their ability to compete with the binding of [$^3$H]17α,21-dimethyl-19-nor-4,9-pregnadiene-3,20-dione (R5020) (which is the standard ligand for this receptor, see Philibert et al., Endocrinol, (1974), 94, 627). Many of these steroids did not cause any displacement of the tracer until their added concentration exceeded the $K_d$ of R5020 by a very large factor, for example, 10,000. These compounds, therefore, were not good ligands of the progesterone receptor. However, it has been found that the 16α-iodo and both the E and Z 17α-(2-iodovinyl)analogs of 19-nortestosterone bind the progesterone receptor with high affinity.

It is accordingly the object of this invention to provide halogenated steroids and γ-emitting halogenated steroids which bind the progesterone receptor and therefore are useful in progesterone receptor assays. This and other objects of the invention will become apparent to those of ordinary skill in this art from the following detailed description in which FIG. 1 shows inhibition of binding of [$^3$H]R5020 to the progesterone receptor by E-17α-[2-iodovinyl]-19-nortestosterone, Z-17α-(2-iodovinyl)-19-nortesterone, 16α-iodo-19-nortestosterone and progesterone;

FIGS. 2A and 2B show saturation analyses of the progesterone receptor by [$^3$H]R5020 and the [$^{125}$I]E-17α analog, and FIG. 3 shows the Scatchard analysis of the progesterone receptor using [$^3$H]R5020 and the [$^{125}$I]E-17α analog.

SUMMARY OF THE INVENTION

This invention relates to certain analogs of 19-nortestosterone and the use thereof. More particularly, the invention relates to the 16α-iodo and 17α-(2-iodovinyl) (both the E and Z isomers) analogs of 19-nortestosterone and their use in progesterone receptor assays. The analogs can be γ-emitting.

DESCRIPTION OF THE PREFERRED EMBODIMENTS

The present invention provides three steroidal compounds which are ligands which bind to the progesterone receptor. These compounds are 16α-iodo-19-nortestosterone(16-α-iodo-4-esterene-17β-ol-3-one; hereinafter referred to as INT), E-17α-[2-iodovinyl]-19-nortestosterone(E-17α-(2-iodovinyl)-4-estrene-17β-ol-3-one; hereinafter referred to EVNT), and Z-17α-(2-iodovinyl)-19-nortestosterone(Z-17α-(2-iodovinyl)-4-estrene-17β-ol-3-one; hereinafter referred to as ZVNT).

The INT can be prepared by halogen exchange with 16β-bromo-19-nortestosterone and the exchange reaction results in an inversion at the 16 position. A typical preparation is set forth in the example below. The EVNT and ZVNT can be prepared by iodinating a mixture of E- and Z-∫α-(2-tri-n-butylstannylvinyl)-4-estrene-17β-ol-3-one which, in turn, is prepared by the reaction of tri-n-butyltin hydride and azobisisobutyronitrile with 17α-ethinyl-19-nortestosterone. To prepare the radioactive EVNT and ZVNT, and E and Z butylstannylvinyl species are separated before the radioiodide is added. Typical preparations are shown in examples 8 and 10 below.

The radiolabelled materials are useful for progesterone receptor assays for determining the binding capacity of cytosol protein. The procedure used in the receptor assay is similar to that conventionally used when the receptor assay is conducted using [$^3$H]5020 as the radiolabelled tracer. One important application is an in vitro assay of breast biopsy tissue to determine its progesterone receptor content, information which is of particular value to a physician in planning future clinical treatment. The non-radiolabelled compounds are useful to displace the radioactive ligands in binding assays so as to measure non-specific binding.

In order to better describe this invention, various examples are set forth below. In these examples, as well as throughout this specification and claims, all parts and percentages (except chromatography solvent mixtures) are by weight and all temperatures are in degrees Centigrade, unless otherwise specified. The composition of chromatography solvent mixtures is given in parts or percentages by volume.

Melting points were obtained in a Koffler Hot Stage or in a Mel-temp apparatus and are uncorrected. Infrared spectra were recorded in potassium bromide discs using a Beckman Acculab 4 spectrophotometer. NMR spectra were obtained with a Varian EM360A spectrometer equipped with EM3630 lock decoupler and V2048 signal averager. Mass spectra were recorded on Hewlett Packard Models 5985A and 5890A spectrometers at 20 ev or 70 ev with a direct insertion probe. High Performance Liquid Chromatography was performed using a Waters modular system consisting of a U6K injector, M-45 pump, and model 440 detector or a Beckman Model 334 gradient system equipped with Model 421 controller, Altex CR-1A integrator-recorder, and Hitachi Model 100-10 variable wavelength detector.

Figure 1:
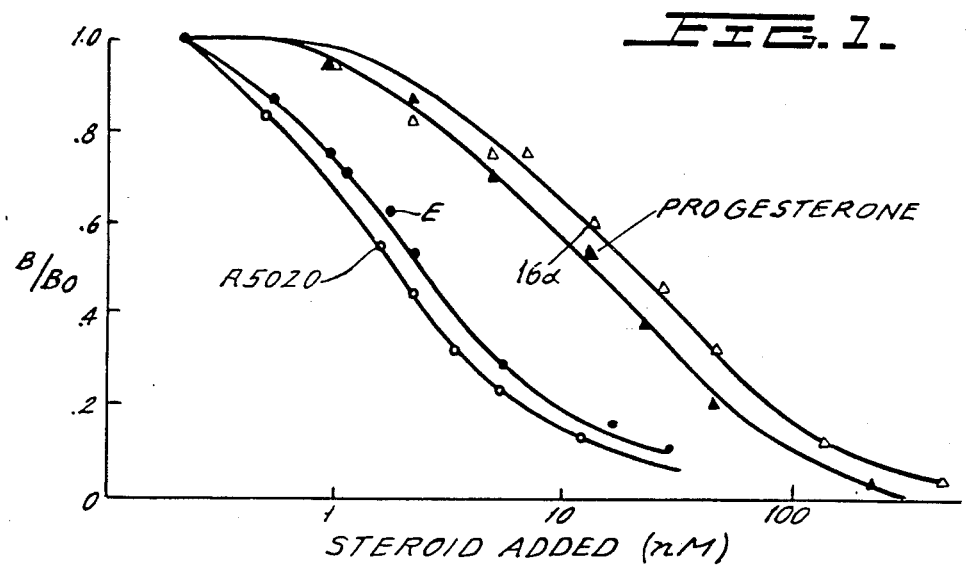

Progesterone receptor assay: A 2.5 kg female rabbit was injected intramuscularly for four successive days with 0.1 mg of estradiol cypionate in 0.1 ml of sesame oil. On the fifth day the uterus was excised, weighed and homogenized at 0° C. in 1.5 volumes of iced buffer containing: 1 mM dithiothreitol, 0.15 mM Na$_2$EDTA, 30% glycerol, 20 mM sodium molybdate, 10 mM Tris/HCl, pH 7.4 (4° C.). Homogenization was accomplished with three 10 second bursts of Polytron homogenizer. The homogenate was centrifuged at 3,000×g for 10 min. and the resulting supernatant was centrifuged at 100,000×g for 1 hour. The final supertant (cytosol) was diluted with homogenization buffer to afford 20–40% binding of a trace of [$^3$H]R5020 (90 Ci/mMol), 10,000 dpm, and 50 μl of the appropriate radioinert compound. Non-specific binding was evaluated in tubes containing 2 μM R5020. After incubating at 4° C. overnight, free and bound steroids were separated by the addition of 100 μl of a stirred suspension of charcoal (5 mg/ml) in 10 mM Tris-HCl, pH 7.4 (4° C.), 0.15 mM Na$_2$EDTA. After mixing and standing on ice for 10 min., the tubes were centrifuged at 1500×g for 10 mins. and the "bound" radioactivity, in a 0.15 ml aliquot of the supernatant, was measured in a liquid scintillation counter. The effect of the competitors on the binding of [$^3$H]R5020 is shown in FIG. 1.

EXAMPLE 1

3,3-Ethylenedioxy-5-estrene-17-one

4-Estrene-17β-ol-3-one(19-nortestosterone), 5 g, was converted in 92% yield to a 2:1 mixture of Δ$^{5(10)}$ and Δ$^5$-3-ethylene ketals according to the method described by Djerassi and coworkers J. Amer. Chem. Soc. (1959) 81, 3120. The ratio of isomers was computed from the ratio of NMR peaks at δ5.4(H-6) δ3.97 (ketal) and δ3.6(H-17δ). Oxidation of this material by chromium trioxide-pyridine complex according to standard methods and chromatography on basic alumina (1% ethylacetate in benzene) gave a 57% yield of the product which was a mixture of the Δ$^{5(10)}$ and Δ$^5$isomers.

EXAMPLE 2

16α-Bromo-3,3-ethylenedioxy-5-estrene-17-one.

A 1.07M solution of lithium diisopropylamide in hexane, 0.98 ml (1.05 mmole), was placed in a dry flask under nitrogen. A solution of 300 mg of 3,3-ethylenedioxy-5-estrene-17-one (0.948 mmole) in 3 ml of dry tetrahydrofuran was added with stirring over 5 mins. After an additional 15 mins., the mixture was cooled in a dry ice-acetone bath, and a solution of 167 mg (1.04 mmole) of bromine in 3.61 ml of methylene chloride was added rapidly. After 5 min., 6 ml of a saturated aqueous solution of NaHCO$_3$ was added and the mixture was slowly allowed to warm to room temperature. The mixture was transferred to a separatory funnel with the aid of 90 ml of ether. The organic phase was washed with three 30 ml portions of water and then dried over anhydrous sodium sulfate. Filtration and evaporation of the solvent gave an oil which was crystallized from methanol to give 180 mg (48% of product. m.p. 157°–163°. I.R. (KBr) 1740 cm$^{-1}$ (strong). NMR(CDCl$_3$) δ5.50 (m, 1, H-6), 4.57 (m, 1, H-16β), 3.97 (s, 4, ketal), 0.95 (s, 3, H-18).

EXAMPLE 3

16β-Bromo-3,3-ethylenedioxy-5-estrene-17-one

Epimerization was achieved by stirring 141 mg of 16α-bromo-3,3-ethylenedioxy-5-estrene-17-one with 360 mg of lithium bromide in 2.9 ml of N,N-dimethylformamide for 19 hours at room temperature. The mixture was pipetted into 150 ml of hot water with stirring. After cooling slowly to 0° C., the resulting precipitate was collected to give 129 mg (91.5%) of the 16β-bromo ketone. NMR analysis indicated this material to be at least 90% 16β-epimer. m.p. 190°–200° I.R. (KBr0, 1752 cm$^{-1}$ strong. NMR (CDCl$_3$) δ5.42 (m, 1, H-6), 4.17 (m, 1, H-6), 4.17 (m, 1, H-16α), 3.98 (s, 4, ketal), 1.1 (s, 3, H-18).

EXAMPLE 4

16β-Bromo-3,3-ethylenedioxy-5-estrene-17β-ol

A mixture of 128.5 mg (0.325 mmole) of the 16β-bromo ketone was stirred with 51 mg (1.34 mmole) of sodium borohydride and 191 ml of absolute ethanol at 4° C. for 20 hours. The mixture was then poured into 110 ml of water at 0° C. and stirred for 1 hour. The resulting precipitate was collected by filtration and amounted to 110.2 mg (85%). I.R. (KBr) 3460 cm$^{-1}$ (broad, 17β-OH), NMR (CDCl$_3$) δ5.47 (m, 1, H-6), 4.57 (m, 1, H-16α), 3.97 (s, 4, ketal), 3.37 (d, 1, H-17α), 0.91 (s, 3H, H-18).

EXAMPLE 5

16β-Bromo-4-estrene-17β-ol-3-one

The protected 16β, 17β bromhydrin, 110.2 mg (0.277 mmole), 38 ml of distilled dioxane, and 9.75 ml of 0.2N HCl were shaken at 37° C. for 22 hours. The mixture was neutralized with 271 μl of triethylamine, evaporated to dryness, and the residue stirred with 50 ml of water at 0° C. This gave a filterable white solid which amounts to 77.4 mg (79%). It was recrystallized from ethanol. m.p. 148°–151°. I.R. (KBr), 3340 cm$^{-1}$ (broad, 17β-OH), 1660 (strong, C=O), 1610 (weak, C=C), NMR (CDCl$_3$) δ5.82 (s, 1, H-4), 4.63 (m, 1, H-16α), 3.40 (d, 1, H-17α), 0.96 (s, 3, H-18), Mass Spectral Data: 352, 354 (15.9, 15.3 Parents), 273 (80.5, M-Br), 255 (13.9 M-Br-H$_2$O), 217 (29.2, M-D ring), 213 (4.8, A ring cleavage-Br-H$_2$O), 110 (23.1 B-ring cleavage).

EXAMPLE 6

16α-Iodo-4-estrene-17β-ol-3-one (16α-Iodo-19-nortestosterone).

Thirty mg (0.085 mmole) of 16β-bromo-4-estrene-17β-ol-3-one, and 127 mg (0.85 mmole) of sodium iodide dissolved in 3 ml of acetone were heated at 60° C. in a closed tube for 20 hours. The mixture was then added to 50 ml of water at 0° C. with stirring. The resulting cloudy solution was extracted with four 20 ml portions of methylene chloride. The organic extracts were combined and washed with 20 ml of 10% sodium thiosulfate, then with three 20 ml portions of water, and dried over anhydrous sodium sulfate. Filtration and evaporation gave an oil. Crystallization was carried out with aqueous methanol to give 20 mg (59%) of a pale yellow, low melting solid. Further crystallization gave needle-like crystals with m.p. 120°–140°. Analysis by high performance liquid chromatography revealed one major component and several minor components (starting material and epimeric products). The major component was successfully separated by preparative chromatography in two systems: 43% THF H$_2$O on 25 cm×4.6 mm Ultrasphere ODS (C-18) at 0.75 ml/min., R$_T$=12 min. and 1% isopropyl alcohol-methylene chloride on 25 cm×4.6 mm Partisil-10 (silica) at 1 ml/mi., R$_T$=14 min., Detector: 280 nm. This gave material which crystallized from aqueous ethanol. m.p. 142°–144°, I.R. (KBr) 3430 cm$^{-1}$ (broad, 17β-OH), 1666 cm$^{-1}$ (strong, C=O), 1610 cm$^{-1}$ (weak, C=C), NMR (CDCl$_3$), δ5.87 (s, 1, H-4), 3.9–4.2 (m, 2, H-16β and H-17α), 0.8 (s, 3H, H-18), Mass Spectral Data: 400 (4.1 Parent), 273 (base, M-I), 255 (19.6, M-I-H$_2$O), 217 (60.6 M-D-ring), 213 (2.8, A ring cleavage-I-H$_2$0), 110 (5.6 B-ring cleavage).

EXAMPLE 7

17α-(2-tri-n-butylstannylvinyl)-4-estrene-17β-ol-3-one

Ten ml of dry benzene and 100 mg (0.335 mmole) of 17β-hydroxy-17β-ethinyl-4-estrene-3-one (17α-ethinyl-19-nortestosterone) were heated at 80° C. with nitrogen slowly bubbling through the mixture for 10 mins. The solution was then cooled to 50° C. Tri-n-butyltin hydride (150 mg, 0.515 mmole) was added by syringe into the emerging stream of nitrogen, followed by 25 mg of azobisisobutyronitrile. The reaction mixture was refluxed under nitrogen with stirring for 24 hours. The solution was evaporated and the residue was iodinated as described in Example 9.

EXAMPLE 8

E and Z-17α-(2-Iodovinyl)-4-estrene-17β-ol-3-one

Iodine, 152 mg (0.6 mmole), dissolved in 4 ml of methylene chloride was added to the solution of 17α-(2-tri-n-butystannylvinyl)-4-estrene-17β-ol-3-one of Example 8. After stirring was continued for 30 min., the mixture was diluted with 10 ml of a solution containing 10% sodium bisulfite and 1% potassium fluoride, and then transferred to a separatory funnel and shaken. After separation of layers, the organic solution was washed with two 10 ml portions of water and dried over anhydrous sodium sulfate. HPLC analysis (25 cm×4.6 mm Partisil PXS Column, Whatman, 0.8% isopropanol in methylene chloride, 1 ml/min.) of this solution showed the presence of 34% of the E-isomer of the product, 14% of the Z-isomer and 46% of unreacted 17α-ethinyl-19-nortestosterone. Preparative HPLC was conducted on the mixture using a 25 cm×1 cm, Silica Column, Rainin (0.8% isopropanol in methylene chloride, 5 ml/min.). After two additional repurifications under these conditions, the pure isomers were obtained. E-17α-(2-iodovinyl)-4-estrene-17β-ol-3-one: m.p. 111°–114° d; I.R. (KBr) 3425 cm$^{-1}$ (broad, 17β-OH), 1660 (C=O), 1620 (C=C), 965 (trans-CH=CH-out of plane), NMR (CDCl$_3$): δ6.7 and 6.2 (AB pattern, 2, trans-CH=CH-, J=15.2 Hz), 5.84 (s, 1, H-4), 0.97 (s, 3, H-18), Mass Spectral Data: 426 (10.2, Parent), 299 (base, M-I), 281 (22.6, M-I-H$_2$O), 231 (34.4 A-ring cleavage-17α-side chain). Z-17α-(2-iodovinyl)-4-estrene-17β-ol-3-one: m.p. 117°–118° d; I.R. (KBr pellet): 3430 cm$^{-1}$ (broad, 17β-OH), NMR (CDCl$_3$), δ6.77 and 6.33 (AB pattern, 2 cis-CH=CH, J=8.6 Hz), 5.83 (s, 1, H-4), 1.01 (s, 3, H-18). Mass Spectral Data: 426 (2.5, Parent), 299 (97.2, M-I), 281 (38.7, M-I-H$_2$O), 231 (base, A-ring cleavage-17α-side chain).

EXAMPLE 9

The progesterone receptor assay described above was carried out and the results are shown in FIG. 1 and Table 1 below. In FIG. 1, B$_o$ is the specifically bound [$^3$H]R5020 alone and b is the specifically bound [$^3$H]R5020 in the presence of the designated concentration of competitor. The curve for ZVNT overlaps portions of the curves for both R5020 and EVNT and has been omitted for clarity. In Table 1 below, the values in parenthesis are the number of complete experiments which were conducted; the binding constants are means±SEM.

TABLE 1

| Binding of Ligands to the Progesterone Receptor | |
|---|---|
| Compound | K$_i$ (× 10$^9$ M) |
| 17α, 21-dimethyl-19-nor-4,9-pregnadiene-3 3,20-dione, R5020 | *1.053 ± 0.19 (5) |
| Z-17α-(2-iodovinyl)-4-estrene-17β-ol-3-one | 1.81 (2) |
| E-17α-(2-iodovinyl)-4-estrene-17β-ol-3-one | 4.26 ± 0.94 (4) |
| Progesterone | 10.4 (2) |
| 16α-Iodo-4-estrene-17β-ol-one | 39.8 (2) |

*K$_d$.

EXAMPLE 10

E-17α-2-[$^{125}$I]iodovinyl)-19-nortestosterone

While a thoroughly dried 13×100 mm test tube equipped with a screw cap was being constantly swept with a stream of N$_2$, the following were added: 10 mg (33.6 μmol) of 17α-ethinyl-19-nortestosterone, 25 mg of 2,2'-azobisisobutyronitrile, 1 ml of dry, freshly distilled benzene and 15 mg (13.8 μl, 50.4 μmole) of tri-n-butyltin hydride. The tube was sealed and heated for 21 hr. at 80° C. in a thermostated heating block. The reaction mixture was allowed to cool to room temperature and a small aliquot analyzed by high performance liquid chromatography (HPLC) with system A: 25 cm×4.6 cm Partisil-100 column (Whatman Co) with 0.5% isopropanol in CH$_2$Cl$_2$ at 1 ml/min. In this system Z-17α-(2-tri-n-butylstannylvinyl)-19-nortestosterone elutes in 8.2 min, the E-isomer in 9.9 min., and the starting material, 17α-ethinyl-19-nortestosterone in 21.4 min. The yield of the reaction, as determined in the HPLC UV detector at 254 nm, was usually about 10% E-isomer and 5% Z-isomer. (If necessary this mixture could be kept for several weeks at −20° C.) A 200 μl aliquot of the reaction mixture, equivalent to 0.74 μmole of E-isomer, was purified by HPLC as above, and the fraction containing the E-isomer, which eluted at approx. 10 min., was collected.

The synthesis with radioiodide was carried out in an enclosed hood outfitted with charcoal filters. A solution of 4 mCi (1.8 mmol) of [$^{125}$I]NaI (low pH, New England Nuclear Nuclear Co.) was added to a 300 μl Microflex reaction vial (Kontes Glass Co.) containing 2.2 μg (15 mmol) of non-radioactive NaI in 2.2 μl H$_2$O (final specific activity approx. 235 Ci/mmol). The addition of non-radioactive NaI is not necessary but, for these initial studies, allowed accurate determination of the specific activity of the final product by UV absorption on the HPLC. In order to convert any radioactive I$_2$ produced by air oxidation into iodide, 10 μl of an ethanolic solution containing 2.5 μg of NaBH$_4$ was added to the vial and allowed to react for 10 min. While many reducing agents can serve in this manner, NaBH$_4$ was chosen because it is easily destroyed in the following step. The aqueous mixture was diluted with 100 μl of 2-butanone, warmed to approx. 40° C. and dried under a stream of N$_2$. This azeotropic evaporation was repeated once more to ensure removal of all the H$_2$O. The resulting residue was dissolved in 100 μl of acetone and the vial was closed with a cap containing a teflon septum. Chloramine T, 20 μg, (71 nmol) was injected into the vial in 4 μl of tetrahydrofuran (THF). The fraction from the HPLC (described above) containing the E-isomer of the tin adduct (0.74 μmole) was evaporated, the residue dissolved in 100 μl of CH$_2$Cl$_2$ and injected into the sealed vial. The reaction mixture was left to stand for 30 min. at room temp., and then quenched with 100 μl of an aqueous solution containing 10 mg of sodium bisulfite and 1 mg of KF.

After termination of the reaction, the contents of the vial were transferred to a 16 mm×100 mm screw capped test tube with 4 ml of CH$_2$Cl$_2$. The aqueous layer was removed with a pipet and the organic phase was washed 3 times with 1 ml portions of H$_2$O. The organic solution was dried over anhydrous sodium sulfate, transferred to a 10 mm×7.5 cm test tube, and evaporated to dryness in a stream of N$_2$. The residue was dissolved in 100 μl of THF, diluted with 100 μl of H$_2$O and purified by HPLC with system B: 25 cm×4.6 mm μ-Bondapak C-18 column (Waters Co.) with 43% THF in H$_2$O at a flow rate of 1 ml/min. The effluent was monitored at 254 nm. One ml fractions were collected and their content of [$^{125}$I] was determined. Aside from a large amount of polar radioactivity in the solvent front, most of the radioactivity eluted as a symmetrical peak ([$^{125}$I]EVNT) at 24 min. In addition, a much smaller amount of radioactivity eluted at 36 min., the region in which ZVNT migrates. The fractions containing [$^{125}$I]EVNT were combined, diluted with acetonitrile and evaporated under vacuum. The residue was rechromatographed using HPLC system A (described above). In this system there was a single radioactive peak of [$^{125}$I]ENVT at 19 min. (The Z-isomer, which was not present, elutes in 15 min. in this system.) The appropriate fractions were combined, evaporated and dissolved in 20 ml of 10% ethanol in benzene. The total radioactivity, $1.89 \times 10^9$ cpm ($2.7 \times 10^9$ dpm), represented a radiochemical yield of 31%. The steroidal mass was quantified by comparison of the UV peak detected in the HPLC flow cell to standards of EVNT. The specific activity, 220 Ci/mmol, agreed closely with that calculated from the addition of the carrier NaI, 235 Ci/mmol. The specific activity in other experiments ranged from 86 to 220 Ci/mmol.

The radioactive product, [$^{125}$I]EVNT, was stored at 4° C. in the alcoholic benzene solution. Analysis by thin layer chromatography (silica gel:Benzene/ethyl acetate 3:1, R$_f$0.6) showed the material to be stable under these conditions for a period of at least 2-3 months.

Figure 3:
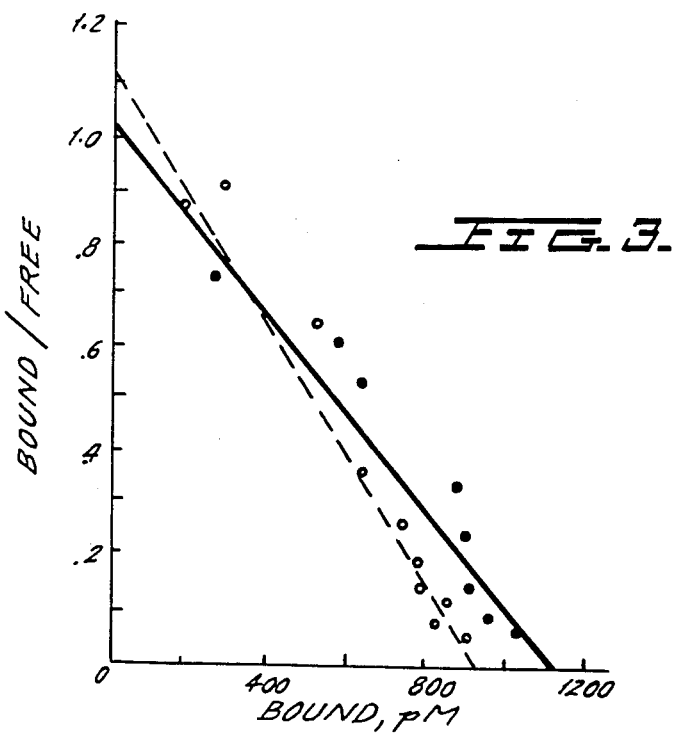

The binding of [$^{125}$I]EVNT to the progesterone receptor was compared to [$^3$H]R5020 using estrogen simulated rabbit uterine cytosol as the source of the receptor. The major results of these studies are shown in FIGS. 2 and 3. Note that both the slope and the intercept of the Scatchard plots, i.e. -Ka and the binding capacity for both R5020 and EVNT are almost the same (FIG. 3). Further, the level of non-specific binding with EVNT is satisfactory and almost identical to that seen with R5020 (FIGS. 2A and 2B).

Association constants and binding capacities determined in five separate experiments with 3 different batches of [$^{125}$I]EVNT showed: Ka=$9.49 \times 10^8 \pm 3.64 \times 10^8$ L/M (SEM) and binding capacity=$9.21 \times 10^{-10} \pm 3.57 \times 10^{-10}$M. In these experiments for [$^3$H]R5020: Ka=$1.25 \times 10^9 \pm 2.92 \times 10^8$ L/M and binding capacity×$6.66 \times 10^{-10} \pm 1.98 \times 10^{-10}$M. Comparison of the association constants and binding capacities for both compounds showed no statistically significant differences.

To be sure that [$^{125}$I]EVNT and [$^3$H]R5020 bound with similar specificities, experiments were performed in which a series of steroids competed with the two differently labelled ligands. The results of this experiment are shown in Table 2. It is apparent that androgens (5α-dihydrotestosterone, testosterone), corticoids (dexamethasone, cortisol), and an estrogen (estradiol), are all ineffective in competing for sites with either ligand. The only substantial competition occurs with the 3 compounds known to be ligands for this receptor, progesterone, R-5020 and EVNT.

TABLE 2

| Competition For the Progesterone Receptor | | | | |
|---|---|---|---|---|
| | \multicolumn{4}{c}{B/B$_o$ × 10$^2$} |
| | [$^3$H]R5020 | | [$^{125}$I]EVNT | |
| Competitor | 3 nM | 100 nM | 3 nM | 100 nM |
| EVNT | 42 | 0 | 74 | 0 |
| R5020 | 34 | 0 | 74 | 0 |
| Progesterone | 94 | 37 | 91 | 22 |
| 5α-DHT* | 101 | 95 | 100 | 91 |
| Testosterone | 100 | 105 | 101 | 98 |
| Estradiol | 99 | 97 | 105 | 94 |
| Dexamethasone | 103 | 101 | 96 | 100 |
| Cortisol | 98 | 106 | 100 | 102 |

*5-dihydrotestosterone
Each compound, at the two indicated concentrations, was allowed to compete with both [$^3$H]R5020 (0.67 nM) and [$^{125}$I]EVNT (0.18 nM) for sites in rabbit uterine cytosol. B$_o$ is dpm specifically bound when only radioactive steroid was present. B is dpm bound in the presence of competitor.

The theoretical maximum specific activity of [$^{125}$I]EVNT is approximately 2200 Ci/mMol. It was decided, in these initial studies, to synthesize material of lower specific activity so as to be able to determine accurately the specific activity of the final product using a physical method, UV absorption. There is no theoretical or practical reason to prevent the synthesis of carrier free [$^{125}$I]EVNT using this procedure.

The method described in the foregoing example can be employed, with slight modification, to produce the Z isomer which has somewhat greater affinity for the progesterone receptor. This is shown in Example 10.

Various changes and modifications can be made in this invention without departing from the spirit and scope thereof. The various embodiments which have been disclosed herein were for the purpose of further illustrating the invention but were not intended to limit it.

What is claimed is:

1. A γ-emitting progesterone receptor ligand selected from the group consisting of 16α-iodo-19-nortestosterone and 17α-[2-iodovinyl]-19-nortestosterone, in which the said iodo substituent is radioactive.

2. The progesterone receptor ligand in accordance with claim 1 which is E-17α-[2-iodovinyl]-19-nortestosterone.

3. The progesterone receptor ligand of claim 1 which is Z-17α-[2-iodovinyl]-19-nortestosterone.

4. The progesterone receptor ligand of claim 1 which is 16-α-iodo-19-nortestosterone.

5. A progesterone receptor ligand selected from the group consisting of 16α-iodo-19-nortestosterone and 17α-[2-iodovinyl]-19-nortestosterone.

6. The progesterone receptor ligand in accordance with claim 5 which is E-17α-[2-iodovinyl]-19-nortestosterone.

7. The progesterone receptor ligand of claim 5 which is Z-17α-[2-iodovinyl]-19-nortestosterone.

8. The progesterone receptor ligand of claim 5 which is 16-α-iodo-19-nortestosterone.

9. In an in vitro method for the determination of the progesterone receptor in which a sample is contacted with a radioactive progesterone receptor ligand and the radioactivity bound to the sample is determined, the improvement which comprises employing the γ-emitting progesterone receptor ligand of claim 1 as said ligand.

10. The method of claim 9 in which said ligand is E-17α-[2-iodovinyl]-19-nortestosterone.

11. The method of claim 9 in which said ligand is Z-17α-[2-iodovinyl]-19-nortestosterone.

12. The method of claim 9 in which said ligand is 16-α-iodo-19-nortestosterone.

13. The method of claim 9 in which said sample is breast biopsy tissue.

14. A kit for use in carrying out the method of claim 9 comprising a container of reagent, said reagent being a progesterone receptor ligand selected from the group consisting of 16α-iodo-19-nortestosterone and 17α-[2-iodovinyl]-19-nortestosterone, in which the said iodo substitutent is radioactive.

15. The kit of claim 14 in which said ligand is E-17α-[2-iodovinyl]-19-nortestosterone.

16. The kit of claim 14 in which said ligand is Z-17α-[2-iodovinyl]-19-nortestosterone.

17. The kit of claim 14 in which said ligand is 16-α-iodo-19-nortestosterone.

18. The kit of claim 14 in which said reagent and a carrier thereof are in said container.

* * * * *

UNITED STATES PATENT AND TRADEMARK OFFICE
CERTIFICATE OF CORRECTION

PATENT NO. : 4,780,420
DATED : October 25, 1988
INVENTOR(S) : Richard HOCHBERG, et al.

It is certified that error appears in the above-indentified patent and that said Letters Patent is hereby corrected as shown below:

TITLE PAGE:

After "[73] Assignee: Yale University, New Haven, Conn.", insert --;St. Luke's-Roosevelt Hospital Center, New York, New York; and Research Foundation of the State University of New York, Albany, New York--.

Signed and Sealed this

Twenty-eighth Day of October, 1997

Attest:

BRUCE LEHMAN

*Attesting Officer*     *Commissioner of Patents and Trademarks*